(12) United States Patent
Yoshida et al.

(10) Patent No.: US 9,933,436 B2
(45) Date of Patent: Apr. 3, 2018

(54) METHOD OF EVALUATING CELLULITE AND METHOD OF EVALUATING CELLULITE-EFFECTIVE DRUG USING FIBULIN-3 AND/OR SARCOGLYCAN GAMMA AS AN INDICATOR

(75) Inventors: Yuzo Yoshida, Yokohama (JP); Kentaro Kajiya, Yokohama (JP); Michael Detmar, Boppelsen (CH)

(73) Assignees: Shiseido Company, Ltd., Tokyo (JP); ETH Zurich, Zurich (CH)

( * ) Notice: Subject to any disclaimer, the term of this patent is extended or adjusted under 35 U.S.C. 154(b) by 0 days.

(21) Appl. No.: 14/426,404

(22) PCT Filed: Sep. 7, 2012

(86) PCT No.: PCT/JP2012/073561
§ 371 (c)(1),
(2), (4) Date: Mar. 6, 2015

(87) PCT Pub. No.: WO2014/038097
PCT Pub. Date: Mar. 13, 2014

(65) Prior Publication Data
US 2015/0301064 A1 Oct. 22, 2015

(51) Int. Cl.
*G01N 33/68* (2006.01)
*C12Q 1/68* (2006.01)
*G01N 33/50* (2006.01)

(52) U.S. Cl.
CPC ....... *G01N 33/6881* (2013.01); *C12Q 1/6881* (2013.01); *G01N 33/5044* (2013.01); *C12Q 2600/136* (2013.01); *C12Q 2600/158* (2013.01); *G01N 2333/4703* (2013.01); *G01N 2500/10* (2013.01); *G01N 2800/20* (2013.01)

(58) Field of Classification Search
None
See application file for complete search history.

(56) References Cited

U.S. PATENT DOCUMENTS

| | | | | |
|---|---|---|---|---|
| 5,962,482 A * | 10/1999 | Bissett | ............ | A61K 8/675 514/356 |
| 6,953,583 B1 * | 10/2005 | Ghisalberti | ............ | A23L 1/3002 424/401 |
| 7,569,221 B2 * | 8/2009 | Li | ............ | C12Q 1/6886 424/93.21 |
| 2006/0094054 A1 * | 5/2006 | Schiemann | ............ | C12Q 1/6886 435/6.16 |
| 2009/0220488 A1 * | 9/2009 | Gardner | ............ | C07K 16/18 514/1.1 |

OTHER PUBLICATIONS

Seeliger et al. (2009) EFEMP1 Expression Promotes In vivo Tumor Growth in Human Pancreatic Adenocarcinoma. Molecular Cancer Research, 7(2):189-198.*
Kruglikov, I. (2012) The Pathophysiology of Cellulite: Can the Puzzle Eventually Be Solved? Journal of Cosmetics, Dermatological Sciences and Applications, 2:1-7.*
Rawlings, A. V. (2006) Cellulite and its treatment. International Journal of Cosmetic Science, 28:175-190.*
Liang et al. (2002) Analysis of Gene Induction in Human Fibroblasts and Bladder Cancer Cells Exposed to the Methylation Inhibitor 5-Aza-2_-deoxycytidine. Cancer Research, 62:961-966.*
Yoshida et al. (2014) Histological studies and laser capture microdissection of cellulite tissue reveal decreased expression of EFEMP1 and new mechanisms leading to cellulite. 28th IFSCC, 10 pages.*
Dimri et al., "A biomarker that identifies senescent human cells in culture and in aging skin in vitro," Proc. Natl. Acad. Sci. USA, Sep. 1995, 92:9363-9367.
Hack et al., "γ-Sarcoglycan Deficiency Leads to Muscle Membrane Defects and Apoptosis Independent of Dystrophin," The Journal of Cell Biology, Sep. 7, 1998, 142(5):1279-1287.
McLaughlin et al., "Lack of fibulin-3 causes early aging and herniation, but not macular degeneration in mice," Human Molecular Genetics, Jan. 1, 2007, 16(24):3059-3070.
Rona et al., "Testing anticellulite products," International Journal of Cosmetic Science, Jun. 1, 2006, 28(3):169-173.
Sercu et al., "ECM1 interacts with fibulin-3 and the beta 3 chain of laminin 332 through its serum albumin subdomain-like 2 domain," Matrix Biology, Apr. 1, 2009, 28(3):160-169.
Yanagisawa et al., "Unraveling the mechanism of elastic fiber assembly: The roles of short fibulins," The International Journal of Biochemistry & Cell Biology, Jul. 1, 2010, 42(7):1084-1093.

* cited by examiner

*Primary Examiner* — Neil P Hammell
(74) *Attorney, Agent, or Firm* — Foley & Lardner LLP

(57) ABSTRACT

The present invention relates to a method of evaluating cellulite using fibulin-3 and/or sarcoglycan gamma as an indicator in a harvested skin sample, and a method of evaluating a drug for improving, preventing or treating cellulite using fibulin-3 and/or sarcoglycan gamma as an indicator in cultured cells.

10 Claims, 9 Drawing Sheets

```
                        SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: G3PDH forward primer

<400> SEQUENCE: 1
gagtcaacgg atttggtcgt                                              20

<210> SEQ ID NO 2
<211> LENGTH: 20
<212> TYPE: DNA
<213> ORGANISM: Artificial Sequence
<220> FEATURE:
<223> OTHER INFORMATION: G3PDH reverse primer

<400> SEQUENCE: 2
tgggatttcc attgatgaca                                              20

<210> SEQ ID NO 3
<211> LENGTH: 20
<212> TYPE: DNA
<213> ORGANISM: Artificial Sequence
<220> FEATURE:
<223> OTHER INFORMATION: 18S rRNA forward primer

<400> SEQUENCE: 3
cggctaccac atccaaggaa                                              20

<210> SEQ ID NO 4
<211> LENGTH: 18
<212> TYPE: DNA
<213> ORGANISM: Artificial Sequence
<220> FEATURE:
<223> OTHER INFORMATION: 18S rRNA reverse primer

<400> SEQUENCE: 4
gctggaatta ccgcggct                                                18

<210> SEQ ID NO 5
<211> LENGTH: 25
<212> TYPE: DNA
<213> ORGANISM: Artificial Sequence
<220> FEATURE:
<223> OTHER INFORMATION: Fibulin-3 forward primer

<400> SEQUENCE: 5
gcttccgttg ttatccacga aatcc                                        25
```

```
<210> SEQ ID NO 6
<211> LENGTH: 25
<212> TYPE: DNA
<213> ORGANISM: Artificial Sequence
<220> FEATURE:
<223> OTHER INFORMATION: Fibulin-3 reverse primer

<400> SEQUENCE: 6
ctgtatctgg aagatgtctg atggc                                  25

<210> SEQ ID NO 7
<211> LENGTH: 25
<212> TYPE: DNA
<213> ORGANISM: Artificial Sequence
<220> FEATURE:
<223> OTHER INFORMATION: Sarcoglycan gamma forward primer

<400> SEQUENCE: 7
gaggccagag aatcagtatg tctac                                  25

<210> SEQ ID NO 8
<211> LENGTH: 26
<212> TYPE: DNA
<213> ORGANISM: Artificial Sequence
<220> FEATURE:
<223> OTHER INFORMATION: Sarcoglycan gamma reverse primer

<400> SEQUENCE: 8
ccatcttttg ttacacacaa gtggcc                                 26
```

METHOD OF EVALUATING CELLULITE AND METHOD OF EVALUATING CELLULITE-EFFECTIVE DRUG USING FIBULIN-3 AND/OR SARCOGLYCAN GAMMA AS AN INDICATOR

CROSS-REFERENCE TO RELATED APPLICATIONS

This application is a National Stage application of PCT/JP2012/073561, filed Sep. 7, 2012.

The instant application contains a Sequence Listing which has been submitted in ASCII format via EFS-WEB and is hereby incorporated by reference in its entirety. Said ASCII copy, created on Apr. 30, 2015, is named sequence.txt and is 2 KB.

TECHNICAL FIELD

The present invention relates to a method of evaluating cellulite and a method of evaluating a cellulite-effective drug using fibulin-3 and/or sarcoglycan gamma as an indicator.

BACKGROUND ART

"Cellulite" (also named gynoid lipodystrophy) is a tissue that exhibits a rippled appearance of the skin mainly observed in the abdomen, thigh and buttock of women, and is especially a cosmetic problem, since it markedly impairs skin appearance. The pathogenesis of cellulite has not been fully elucidated academically or medically, and it is simply considered to be an accumulation of subcutaneous fat. According to a noninvasive analysis using MRI conducted by Mirrashed, F. and Querleux, B et al., morphological changes of adipose cells and adipose tissues were not observed in cellulite skin, but in cellulite skin, it was revealed that a part of the subcutaneous fat tissues projected deeply into the dermal layer (Non-patent Literature 1 and 2).

Since 40% of adult women have cellulite, and cellulite significantly impairs aesthetic appearance, there is a high demand for alleviating, preventing and treating cellulite, and products and aesthetic treatments intended for cellulite are already on the market both domestically and abroad. However, since the histological characteristics defining cellulite and the formation mechanism thereof have not been elucidated, such products are usually directed to a product lacking effective data or simply slimming agents intended to reduce the amount of fat. Thus, there is very little at present that is really effective for reducing, preventing and treating cellulite, and no products specifically targeted for cellulite have been commercially available yet.

Although there are few references disclosing drugs and/or treatments for improving the appearance of cellulite along with experimental data on them, nicotinamide, conjugated linoleic acid and sulfocarbiose are disclosed as drugs that alleviate cellulite by applying on the affected cellulite site, along with experimental data (Patent Literature 1 and 2, and Non-patent Literature 8), and furthermore 1-4 MHz ultrasonic stimulation is disclosed as a treatment for alleviating cellulite (Patent Literature 3). While these references disclose data indicating the effect of alleviating cellulite, they do not clearly demonstrate its mechanism of action, and thus it is still unknown whether the reduction in cellulite is caused by the reduction in the amount of fat or whether a mechanism other than the reduction in fat works.

Researches on cellulite are mainly carried out by investigating skin tissue by means of noninvasive methods. However, in addition to a problem relating to a small number of test samples due to the nature of noninvasive methods, only fragmented information has been obtained. Thus, it is hardly said that cellulite has been systematically investigated.

CITATION LIST

Patent Literature

[PLT 1] WO99/47112
[PLT 2] WO01/17498
[PLT 3] WO2004/080147

Non-Patent Literature

[NPL 1] Mirrashed, P., et al. (2004). Skin Res Technol 10(3):161-8
[NPL 2] Querleux, B., et al. (2002). Skin Res Technol 8(2): 118-242
[NPL 3] Mine, S., et al. (2008). PLoS One 3(12): e4066
[NPL 4] Ordway, G. A., et al. (2009). J. Neurosci Res 87(11): 2430-8
[NPL 5] Erickson, H. S., et al. (2009). Nat Protoc 4 (6): 902-22
[NPL 6] McLaughlin, P. J., et al. (2007). Hum Mol Genet 16(24): 3059-70
[NPL 7] Rahn, D. D., et al. (2009), Am J Pathol 174 (1): 206-15
[NPL 8] Hack, A. A., et al. (1998). J Cell Biol 142 (5): 1279-87
[NPL 9] Vogelgesang, R., et al. Int J cosmet Sci 33(2): 120-5
[NPL 10] Ana B R R et al., JEADV (2000) 14, 251-262

SUMMARY OF INVENTION

Technical Problem

Under the above circumstances, there is a need for developing a method of evaluating cellulite, a drug intended to improve cellulite, and a method of evaluating such a drug.

Solution to Problem

For the purpose of elucidating the histological characteristics and the formation mechanism of cellulite, more specifically of understanding the phenomena peculiar to cellulite on the tissue level using a variety of cellulite tissue and skin tissue, and furthermore for the purpose of elucidating the mechanism of appearance of the phenomena peculiar to cellulite using a molecular biological method, the present inventors have conducted research.

More specifically, 25 samples of skin biopsy tissues (hereinafter referred to as the cellulite skin) from the buttocks and the thighs of females exhibiting cellulite, and 19 samples of skin biopsy tissues (hereinafter referred to as the female control skin) from the buttocks and the thighs of females exhibiting no cellulite, were subjected to tissue analysis by using hematoxyline eosin stain, Sirius Red stain and Elastica van Gieson stain.

This tissue analysis revealed that the papillary structure was significantly reduced in the cellulite skin, that the papillary dermis layer at the upper part of the dermis layer in the cellulite skin was thin compared to the female control skin, that while no marked changes were noted in the amount of collagen fibers containing collagen in cellulite, elastin fibers tended to be decreased and disturbed, and that while no morphological changes were found in the adipose cells and adipose tissues per se in the cellulite skin, localized changes in the form of fat projections were observed.

From the new histological findings mentioned above, it was deduced that the cause of cellulite is twofold: the formation of fat projections inside the skin caused by the increased amount of fat, and changes such as the reduced elasticity and thinning of the dermis which otherwise should play a role of a cushion against the above projections, leading to the outward manifestation of ripples within the skin. Thus, it was found that cellulite formation may be associated with not only localized changes such as protruded fat but also changes in the dermis layer which so far attracted no attention. Therefore, a new finding was obtained which indicates that slimming drugs intended for weight reduction or burning of fat are insufficient for improving cellulite whereas effective drugs or treatments coping with dermal changes may be required for cellulite improvement.

In order to clarify the cause of changes in dermal fibers between the cellulite skin and the female control skin, the present inventors analyzed the expression level of genes of dermal fibroblasts, which constitute the most important cells of the dermis and determine the property thereof. More specifically, since analysis using RNA derived from the full-layer human tissue cannot precisely identify the properties of fibroblasts due to a kind of noise by cells and/or organs other than the fibroblasts that constitute the majority of the full-layer skin, the present inventors have used a Laser capture microdissection method (Non-patent Literature 4 and 5) to extract mRNA of dermal fibroblasts from skin tissue sections, and then gene microarrays have been carried out. As a result, the present inventors have succeeded in identifying a plurality of genes, the expression level of which vary between the cellulite skin and the female control skin.

As a result of specifically examining the expression in the fibroblasts of the cellulite skin by using quantitative PCR for this plurality of genes, a markedly reduced expression of fibulin-3 and sarcoglycan gamma in the cellulite skin was confirmed (FIGS. 4 and 6), and furthermore a similar trend was observed by immunohistological staining (FIGS. 3 and 5).

Fibulin-3 is one of the extracellular proteins involved in the formation of elastic fibers, and, as a common function, is known to be related to elastin fiber formation. (Non-patent Literature 6 and 7). On the other hand, although the function of sarcoglycan gamma, which is a proteoglycan, in the skin has not been demonstrated, it is known as a common function that sarcoglycan gamma protects sarcolemma from the phenotype of defective-function individuals.

Thus, the reduced expression of fibulin-3 is thought to be involved in the cellulite formation, through the abnormal formation of elastic fibers, specifically elastin fibers, and the reduced expression of sarcoglycan gamma is also thought to be involved in cellulite formation, through the reduced function of protecting the cell membrane in fibroblasts. However, the present invention should not be limited by these mechanisms.

Furthermore, when nicotinamide and conjugated linoleic acid, which are known to improve the cellulite appearance, were added to cultured cells, the present inventors have found that these agents enhanced the expression of fibulin-3 and sarcoglycan in a dose-dependent manner. The present inventors, therefore, concluded that these agents can recover the change in the dermal fiber to normal by enhancing the expression of fibulin-3 and sarcoglycan gamma which has been reduced in the cellulite skin, thereby the cellulite appearance can be improved (FIGS. 7 and 8). In addition, when 1 MHz ultrasonic stimulation, that is known to improve the cellulite appearance, was applied to cultured cells, no changes in the expression of fibulin-3 were found, but the expression of sarcoglycan gamma was enhanced. Therefore, the present inventors have concluded that the change in the dermal fibers of cellulite was recovered to normal through the enhancement of sarcoglycan gamma expression (FIG. 9).

Based on the above research and new findings demonstrated by the present inventors, the present inventors have concluded that the reduced expression of fibulin-3 and sarcoglycan gamma is the cause of cellulite formation, and thus have invented a method of evaluating cellulite using fibulin-3 and/or sarcoglycan gamma as an indicator, and a method of evaluating a drug for reducing, improving, preventing or treating cellulite using fibulin-3 and/or sarcoglycan gamma as an indicator.

Thus, the present invention relates to the followings:

[1] A method of evaluating cellulite using the expression of fibulin-3 and/or sarcoglycan gamma in a harvested skin sample as an indicator.

[2] The evaluation method according to item [1], wherein said skin sample is dermis.

[3] The evaluation method according to item [1] or [2], wherein said skin sample is dermal fibroblasts.

[4] A method of evaluating a drug for improving, preventing or treating cellulite, using fibulin-3 and/or sarcoglycan gamma as an indicator in cultured cells.

[5] The evaluation method according to item [4] comprising the steps of:
 adding a candidate drug to cultured cells;
 determining the expression of fibulin-3 and/or sarcoglycan gamma; and
 comparing the expression of fibulin-3 and/or sarcoglycan gamma in the control with the expression of fibulin-3 and/or sarcoglycan gamma after adding the candidate drug.

[6] The evaluation method according to item [4] or [5] wherein said cultured cells are dermal fibroblasts.

[7] The evaluation method according to any one of items [4] to [6], wherein when the amount expressed of fibulin-3 and/or sarcoglycan was enhanced in the above comparison step, the candidate drug is judged to have a cellulite-suppressing activity.

[8] A method of evaluating a cosmetic method for alleviating cellulite using the amount expressed of fibulin-3 and/or sarcoglycan gamma as an indicator.

[9] The evaluation method according to item [8] comprising the steps of:
 determining the amount expressed of fibulin-3 and/or sarcoglycan gamma in the dermis of the skin before applying the cosmetic method;
 applying the cosmetic method;
 determining the expression of fibulin-3 and/or sarcoglycan gamma in the dermis of the skin after applying the cosmetic method; and
 comparing the expression of fibulin-3 and/or sarcoglycan gamma in the dermis of the skin before and after applying the cosmetic method.

[10] The evaluation method according to item [9] wherein when the expression of fibulin-3 and/or sarcoglycan gamma is enhanced in the above comparison step, the cosmetic method is judged to have a cellulite-suppressing activity.

[11] The evaluation method according to item [10] wherein the determination of the expression of fibulin-3 and/or sarcoglycan gamma in the above dermis of the skin is conducted by quantitative PCR for a sample harvested by laser microdissection.

Advantageous Effects of Invention

The present invention enables appropriately evaluating cellulite in a living body by using the expression of fibulin-3 and/or sarcoglycan gamma as an indicator. Also, by using the expression of fibulin-3 and/or sarcoglycan gamma as an indicator, the evaluation of a drug for the activity of suppressing or reducing cellulite becomes possible, and screening for a drug for treating, preventing or alleviating cellulite is possible.

DESCRIPTION OF EMBODIMENTS

Figure 1:
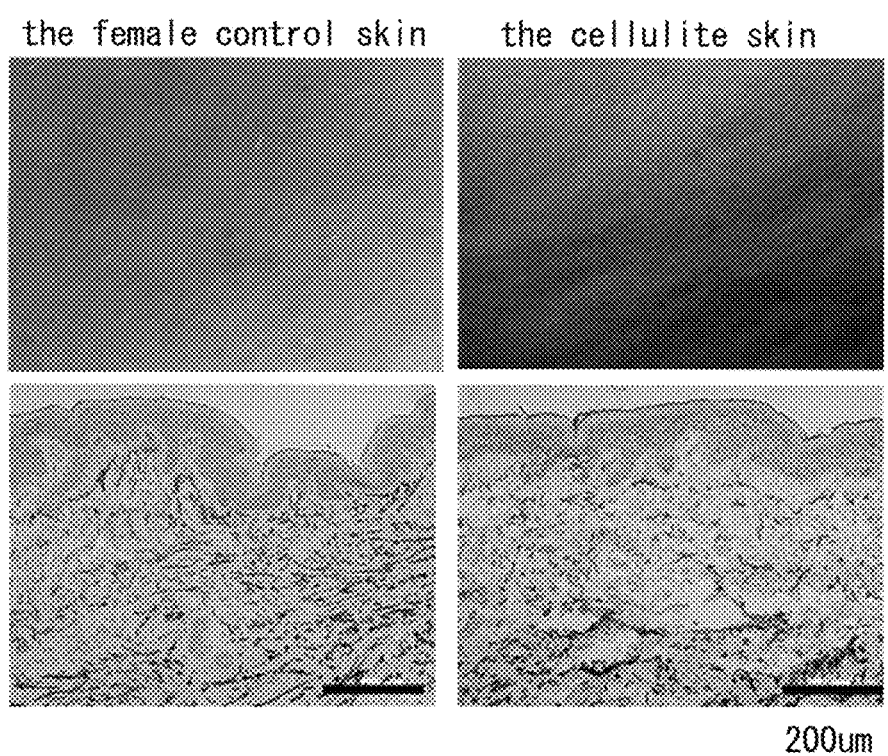
FIG. 1 shows a photo of the appearances of the female control skin and the cellulite skin, and a photo taken by staining the skin section with Elastica van Gieson staining. In the female control skin, elastin fibers are shown to be present densely arranged in the dermis, whereas in the cellulite skin elastin fibers are shown to be aggregated, and present sparsely.

The present invention relates to a method of evaluating cellulite using the expression of fibulin-3 and/or sarcoglycan gamma in a harvested skin sample as an indicator. More specifically, the harvested sample is specifically a dermal tissue, more preferably dermal fibroblasts. The skin sample may be harvested by any method, but in terms of harvesting only the cells of interest, it is preferably harvested by laser microdissection.

The method of evaluating cellulite of the present invention enables to evaluate cellulite in subjects suffering from cellulite of various degrees of severity, by determining the expression of fibulin-3 and/or sarcoglycan gamma in the skin samples obtained from the subjects and clarifying the relationship between the expression and the degree of severity in advance. As the degree of severity of cellulite, a method for classifying cellulite into 0 to 4 grades from the appearance of cellulite (NLP 1). The criteria of classification of the degree of severity of cellulite is as listed in the following table:

TABLE 1

| The severity of cellulite (Grade) | Skin Appearance |
| --- | --- |
| 0 | No dimpling - smooth skin |
| 1 | Low number of small, shallow, visible dimples, sparsely located on the thighs |
| 2 | Moderate number of visible dimples (some large) on the thighs |
| 3 | Large number of visible dimples (many large) over most of the thighs |
| 4 | Cottage cheese appearance of skin |

However, the classification of severity should not be limited to the above classification method, any classification can be used. For example, a method for classifying cellulite which is not based on skin appearance but on the histopathological and clinical observation is also known in the art (NLP10). According to this classification method, the severity of cellulite can be classified as described in the following table:

TABLE 2

| The severity of cellulite (Grade) | Histopathological and Clinical Observation |
| --- | --- |
| 0 | No manifestation of cellulite both in skin appearance and inner skin tissue |
| 1 | The stage wherein there is no manifestation in skin appearance, no clinical change is observed, but several changes occurred in the inner skin |
| 2 | The stage wherein no relief alterations are present at rest, but after skin compression or after muscular contraction, pallor, decreased temperature and/or decreased elasticity is observed |
| 3 | The stage wherein a padded skin and/or an orange peel appearance is evident at rest, and palpable sensation of thin granulations in the deep levels, pain to palpation, decreased elasticity, pallor and/or decreased temperature is observed |
| 4 | The stage wherein there are the same characteristics as in grade III with more palpable, visible and painful nodules, adherence to the deep levels and an obvious wavy appearance of the skin surface |

The evaluation of cellulite in a subject becomes possible by correlating each grade in these classification methods, etc., with the expression level of fibulin-3 and/or sarcoglycan gamma in advance.

By using the expression of fibulin-3 and/or sarcoglycan gamma of the present invention as an indicator, cellulite at an early stage that is not visible on the skin surface can be diagnosed, thereby it is specifically useful in early discovery and prevention of cellulite. If early discovery of cellulite is possible, it enables any preventive measures to be taken before cellulite appears on the skin surface, i.e., before the appearance of the skin is badly affected, and thus it is most preferred.

In another embodiment of the present invention, the present invention relates to a method of evaluating a drug for improving, preventing or treating cellulite by using fibulin-3 and/or sarcoglycan gamma as an indicator in cultured cells. More specifically, said method of evaluating a drug for improving, preventing or treating cellulite may comprise the following steps of:

adding a candidate drug to cultured cells;

determining the expression of fibulin-3 and/or sarcoglycan gamma; and comparing the expression of fibulin-3 and/or sarcoglycan gamma in the control with the expression of fibulin-3 and/or sarcoglycan gamma after adding the candidate drug. Furthermore, when the expression of fibulin-3 and/or sarcoglycan gamma was enhanced, a step of determining that the candidate drug has a cellulite-suppressing activity may be included in or after the comparison step.

The method of the present invention of evaluating a drug for improving, preventing or treating cellulite can be used in screening methods that permit the selection of a candidate drug having a cellulite-decreasing activity by using a candidate drug library containing a variety of candidate drugs, such as a compound library and an extract library. Thus, the method of the present invention of evaluating a drug for improving, preventing or treating cellulite is also directed to a screening method for drugs.

In still another embodiment of the present invention, the present invention also relates to a method of evaluating a cosmetic method for alleviating and/or improving cellulite using fibulin-3 and/or sarcoglycan gamma as an indicator. More specifically, the method of evaluating a cosmetic method comprises the steps of:

determining the expression of fibulin-3 and/or sarcoglycan gamma in the dermis of the skin before applying the cosmetic method;

applying the cosmetic method;

determining the expression of fibulin-3 and/or sarcoglycan gamma in the dermis of the skin after applying the cosmetic method; and comparing the expression of fibulin-3 and/or sarcoglycan gamma in the dermis of the skin before and after applying the cosmetic method. The cosmetic method includes, but not limited to, application of a cosmetic, exercise, massage and ultrasonic treatment. When the expression of fibulin-3 and/or sarcoglycan gamma in the skin dermis, specifically fibroblasts of skin dermis, is enhanced after applying such a cosmetic method in comparison, it may be determined to be effective for alleviating and/or improving cellulite. Such a method of evaluating a cosmetic method may be provided not only by an individual, but also by a cosmetic sales person or an aesthetician other than a physician.

According to the present invention, the expression of fibulin-3 and/or sarcoglycan gamma to be used as an indicator can be determined by any method as long as it can be used in research for gene expression, for example, the determination of the amount of mRNA by quantitative PCR, the determination of the amount of mRNA by Northern blotting, and the determination of the amount of protein by Western blotting, ELISA or immunoprecipitation can be used. From the viewpoint of determining, use of a small amount of a sample harvested by laser microdissection, the determination of mRNA by quantitative PCR may be preferred.

In the method of the present invention, the expression of each of fibulin-3 and sarcoglycan gamma to be used as an indicator may be used individually or both of fibulin-3 and sarcoglycan gamma may be used as an indicator.

According to the present invention, the enhanced expression of fibulin-3 and/or sarcoglycan gamma means that relative to the expression of fibulin-3 and/or sarcoglycan gamma in the control, the expression of fibulin-3 and/or sarcoglycan gamma after adding a candidate drug is increased, preferably by 20% or more, more preferably 35% or more, and most preferably 50% or more. The increase in the expression may preferably be statistically significant.

The dermis is a structure that lies underneath the epidermis, and the epidermis and the dermis are separated by the basal membrane. Fibroblasts are present in the dermis, and anatomically the dermis is composed of two layers of the papillary layer and the reticular layer.

Cultured cells may be any cells as long as they are derived from skin cells. In view of cells related to cellulite, specifically dermal cells, more preferably cultured cells derived from fibroblasts of the dermis are preferred.

EXAMPLES

Example 1

Preparation of Tissue Sections

Tissue analysis was conducted using 25 samples (hereinafter referred to as the cellulite skin) of skin biopsy tissues derived from the buttocks and/or the thighs that exhibit the cellulite appearance, 19 samples (hereinafter referred to as the control skin) of skin biopsy tissues derived from the buttocks and/or the thighs that exhibit no cellulite appearance. All biopsy skin tissues were obtained from women. Biopsy skin tissues were embedded in an embedding medium OCT Compound (Sakura Finetek) for frozen tissues, and frozen-section slides were prepared using a frozen section preparation instrument Cryostat (Leica).

Example 2

Histochemical Staining

Figure 2:
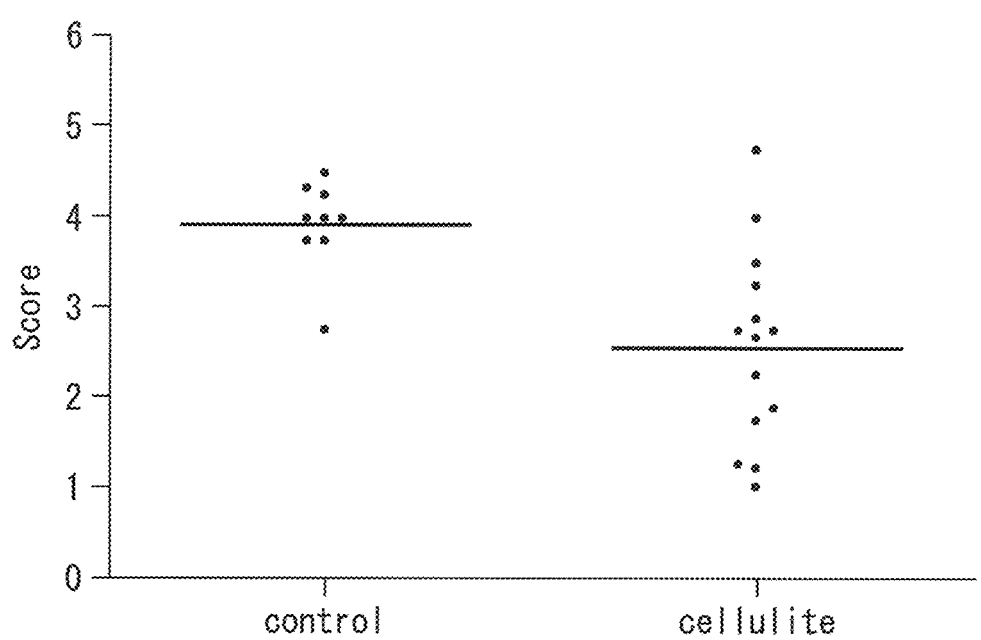
FIG. 2 shows a graph of the degree of arrangement of elastin fibers. Score 1 means that the elastin fibers in photograph are disturbed, and that the amount thereof is low. As the score increases, the elastin fibers are arranged neatly, and the amount thereof are high.

After air-drying the tissue sections obtained in Example 1, each tissue section was subjected to Elastica van Gieson staining using Elastica van Gieson staining reagents (Merck) according to the method described in the instructions. From the result of Elastica van Gieson staining the alignment of elastin fibers in the dermis of cellulite skin was disturbed, and elastin fibers were aggregated and declined in comparison with control skin (FIG. 1). In order to indicate this point obviously, fourteen samples of cellulite tissue sections and nine samples of control tissue sections were selected in random, and then they were scored in a blind trial by two observers. A score was determined to consist of five grades in advance, and when the score was 5, which was the best grade, elastin fibers were determined to be rich and to be aligned neatly in dermis, whereas when the score was 1, which was the lowest grade, elastin fibers were determined to be declined and disarrayed. The average of scores determined by two observers were divided into cellulite group and control group, and plotted respectively to determine tendency of scores. As a result, it was shown that the alignment of elastin fibers in the cellulite group was disturbed, and the elastin fibers in the cellulite group were aggregated and declined (FIG. 2). From these results, the present inventors have concluded that dermal elastin fibers, which should play a role as a cushion against the ripples formed by fat projection in the dermis, are aggregated and reduced, thereby the ripples formed by fat projection in the dermis appear on the surface of skin to form cellulite.

Figure 3:
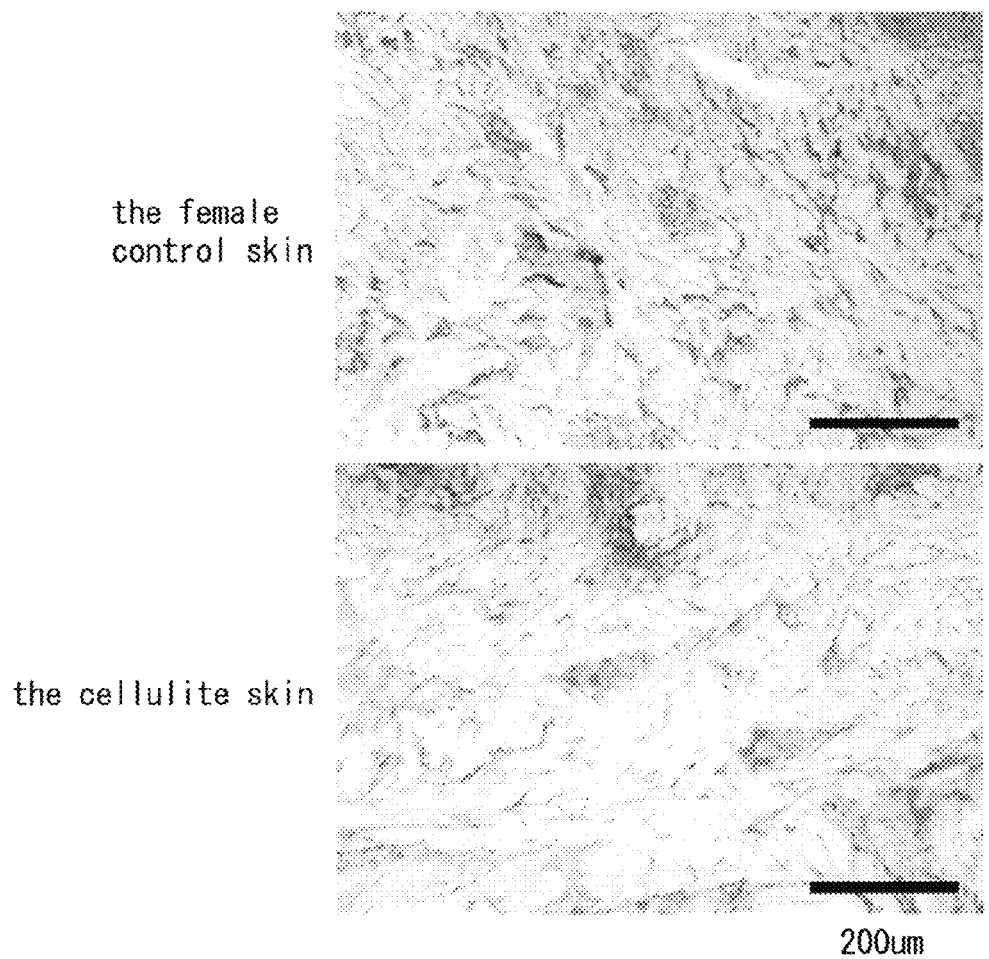
FIG. 3 is a drawing showing immunostaining of fibulin-3 in the dermis. It was shown that the expression of fibulin-3 in the female control skin that does not suffer from cellulite is high, whereas the expression of fibulin-3 in the cellulite skin is low.
Figure 5:
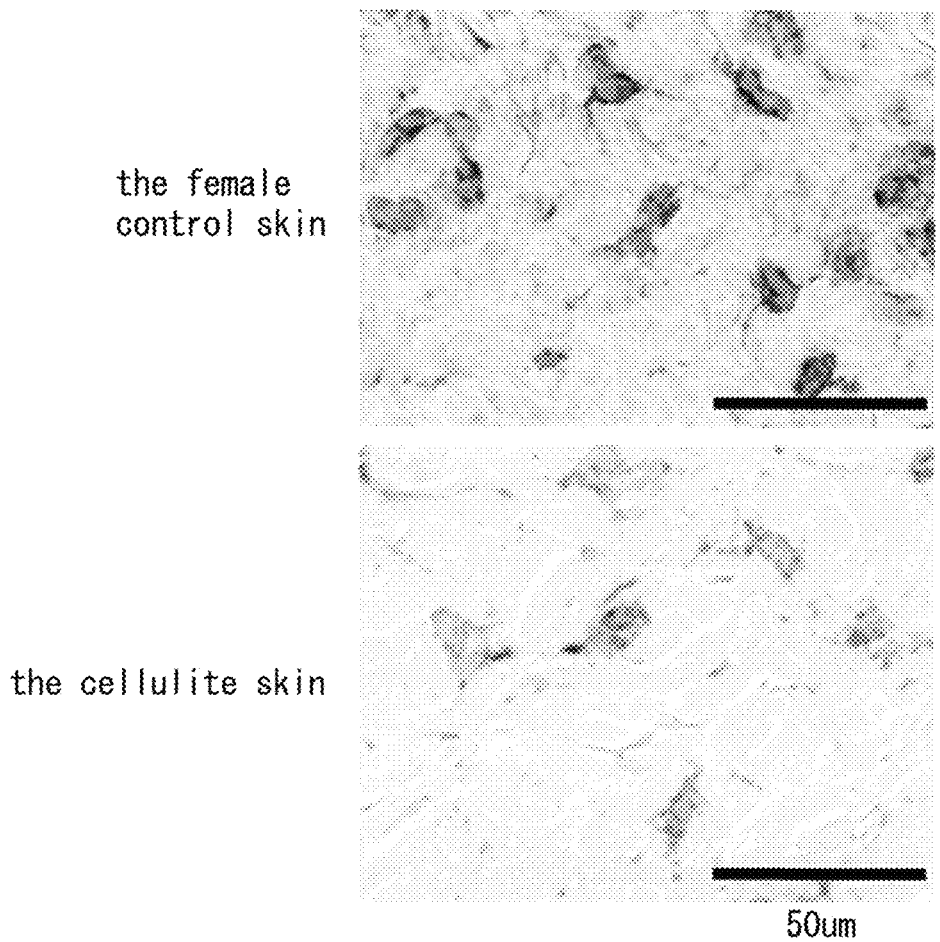
FIG. 5 is a drawing showing immunostaining of sarcoglycan gamma in the dermis. It was shown that the expression of sarcoglycan gamma in the female control skin that does not suffer from cellulite is high, whereas the expression of sarcoglycan gamma in the cellulite skin is low.

After the tissue sections obtained in Example 1 were air-dried, the immunohistological staining of fibulin-3 and sarcoglycan gamma was carried out as follows. After the tissue sections were fixed in 4% PFA for 15 minutes, the tissue sections were washed with PBS, and subjected to immunological staining using CSAII Biotin-free Tyramide Signal Amplification system (DAKO) according to DAKO's protocol. The antibodies used were anti-human fibulin-3 antibody (Santa Cruz) and anti-human sarcoglycan gamma antibody (Abcam). After DAB staining, the sections were mounted with a mounting agent and cover slip, and examined under microscope, such as a fluorescent microscope (Olympus) and photos were taken (FIGS. 3 and 5).

Example 3

Extraction of Trace RNA Derived from Fibroblasts of Skin Tissue Sections, cDNA Synthesis and Amplification Tissue section slides were prepared from tissue sections prepared with a frozen section preparation instrument Cryostat (Leica), by using PEN membrane glass slides (Molecular Device), and then stained using Frozen section staining kit (Arcturus). Subsequently, the tissue section slides were immersed for 30 seconds in 75% ethanol prepared with RNase-free distilled water (hereinafter referred to as the distilled water) immersed for 30 seconds in the distilled water, and then stained for 20 seconds in 100 µl of Histogene staining solution (Arcturus). After washing in the distilled water for 30 seconds, the slides were immersed and dehydrated in a series of 75%, 95% and 100% ethanol, and in xylene for 30 minutes, respectively. The decolorized and dehydrated tissue section slides were set in a laser microdissection instrument Veritas (Arcturus), and areas containing fibroblasts that are single cells localized in the dermis were microdissected while taking care not to contaminate with blood vessels or other auxiliary organs. Subsequently, extraction and purification of trace RNA were carried out by using Rneasy Plus Micro kit (Qiagen). An area of the section containing microdissected fibroblasts was placed in a 500 µl tube containing 350 µl of RLT plus buffer containing 1% mercaptoethanol so as to extract RNA. Then, according to Qiagen's protocol, trace RNA was purified and isolated. After cooling on ice, it was transferred to a cDNA synthesis process. Using the WTOvation Pico System (NuGEN) according to the protocol provided, single stranded cDNA was synthesized based on the extracted RNA as the template, and then amplified. cDNA synthesis and amplification were confirmed by using Bioanalyzer 2100 (Agilent). The concentration was determined by using a nucleic acid quantitation instrument Nanodrop (Thermo Scientific).

Example 4

Quantitative PCR of Fibulin-3 and Sarcoglycan Gamma

Quantitative RT-PCR was carried out by using synthesized cDNA as the template, and further by using a reaction reagent LightCycler (registered trademark) FastStart DNA MasterPlus SYBR Green (Roche), and a reaction instrument LightCycler (Roche) or AB 7900 HT Fast Real-Time PCR System (Applied Biosystems). The condition for composition was as described in Roche's protocol. The annealing temperature of the primers was set at 60° C., and quantitated by using ΔΔCt method.

Sequence information of primer pairs used in Quantitative PCR was as follows:

```
                                             (SEQ ID NO: 1)
G3PDH forward: 5'-GAGTCAACGGATTTGGTCGT-3'

(SEQ ID NO: 2)
reverse: 5'-TGGGATTTCCATTGATGACA-3'

(SEQ ID NO: 3)
18S rRNA forward: 5'-CGGCTACCACATCCAAGGAA-3'

(SEQ ID NO: 4)
reverse: 5'-GCTGGAATTACCGCGGCT-3'

(SEQ ID NO: 5)
Fibulin-3 forward: 5'-GCTTCCGTTGTTATCCACGAAATCC-3'

(SEQ ID NO: 6)
reverse: 5'-CTGTATCTGGAAGATGTCTGATGGC-3'

(SEQ ID NO: 7)
sarcoglycan gamma forward: 5'-GAGGCCAGAGAATCAGTATG
TCTAC-3'

(SEQ ID NO: 8)
reverse: 5'-CCATCTTTTGTTACACACAAGTGGCC-3'
```

Figure 4:
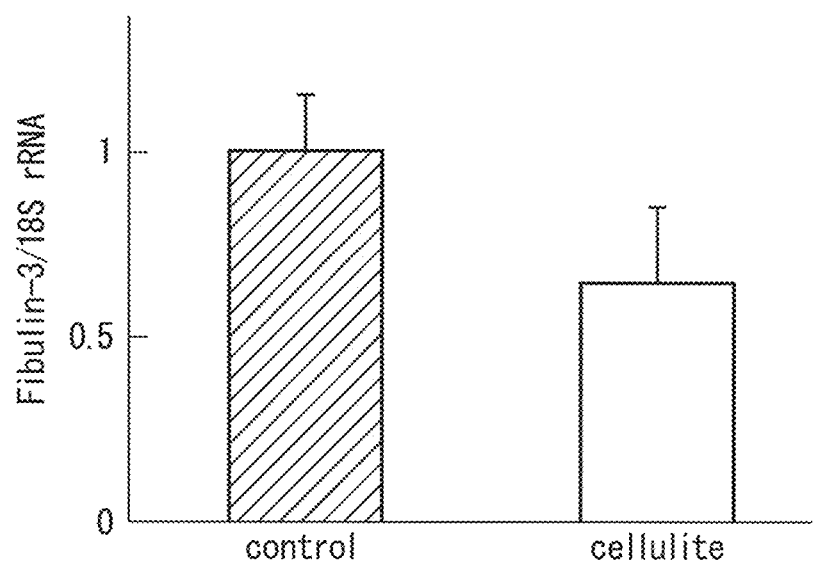
FIG. 4 is a drawing showing the result of determining the amount of mRNA of fibulin-3 in the dermis by quantitative PCR. It was shown that in the female control skin that does not suffer from cellulite the expression of fibulin-3 is high, whereas in the cellulite skin the expression of fibulin-3 is low.
Figure 6:
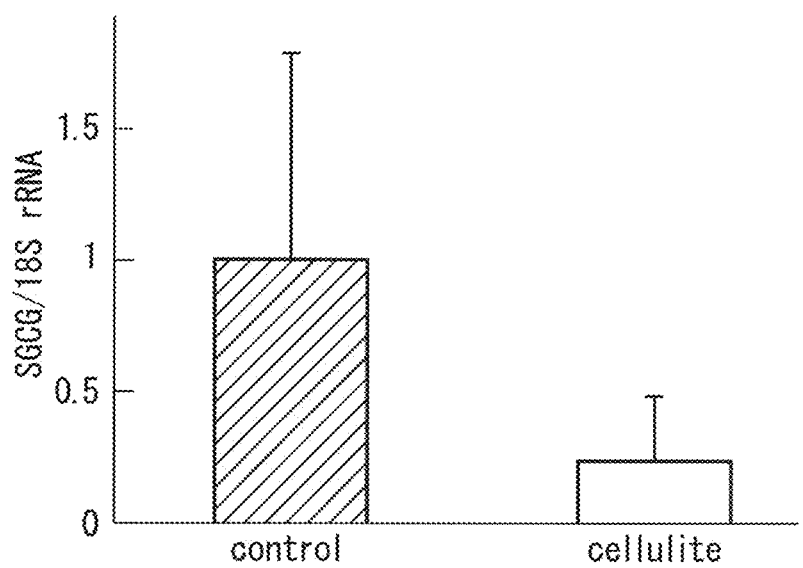
FIG. 6 is a drawing showing the result of determining the amount of mRNA of sarcoglycan gamma in the dermis by quantitative PCR. It was shown that in the female control skin that does not suffer from cellulite the expression of sarcoglycan gamma is high, whereas in the cellulite skin the expression of sarcoglycan gamma is low.

The amount of cDNA in the control group was corrected, and the expression of fibulin-3 and sarcoglycan gamma was compared between the female control skin and the cellulite skin, respectively. The results are shown in FIGS. 4 and 6.

Example 5

Experiment on the Addition of Known Cellulite-improving Drugs

Figure 7:
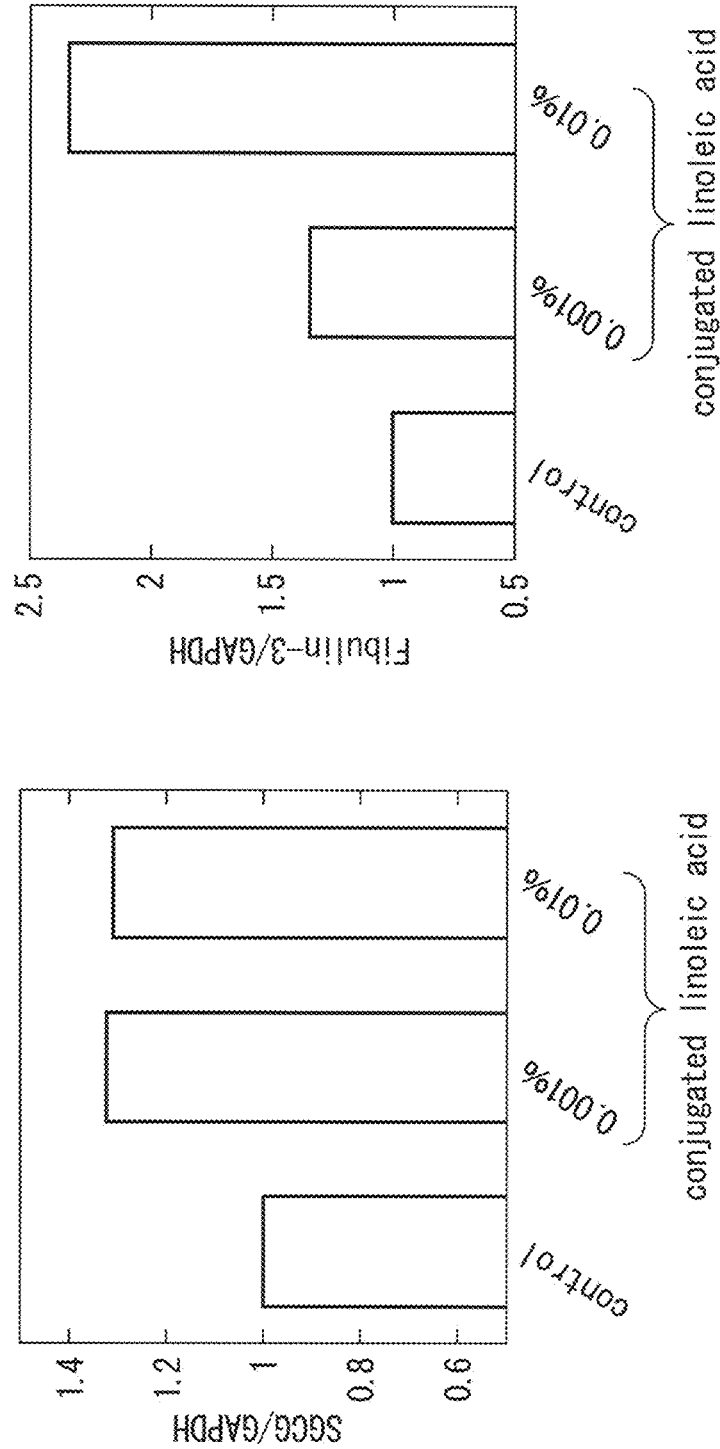
FIG. 7 is a drawing showing changes in the expression of sarcoglycan gamma and fibulin-3 when conjugated linoleic acid was added to cultured fibroblasts.
Figure 8:
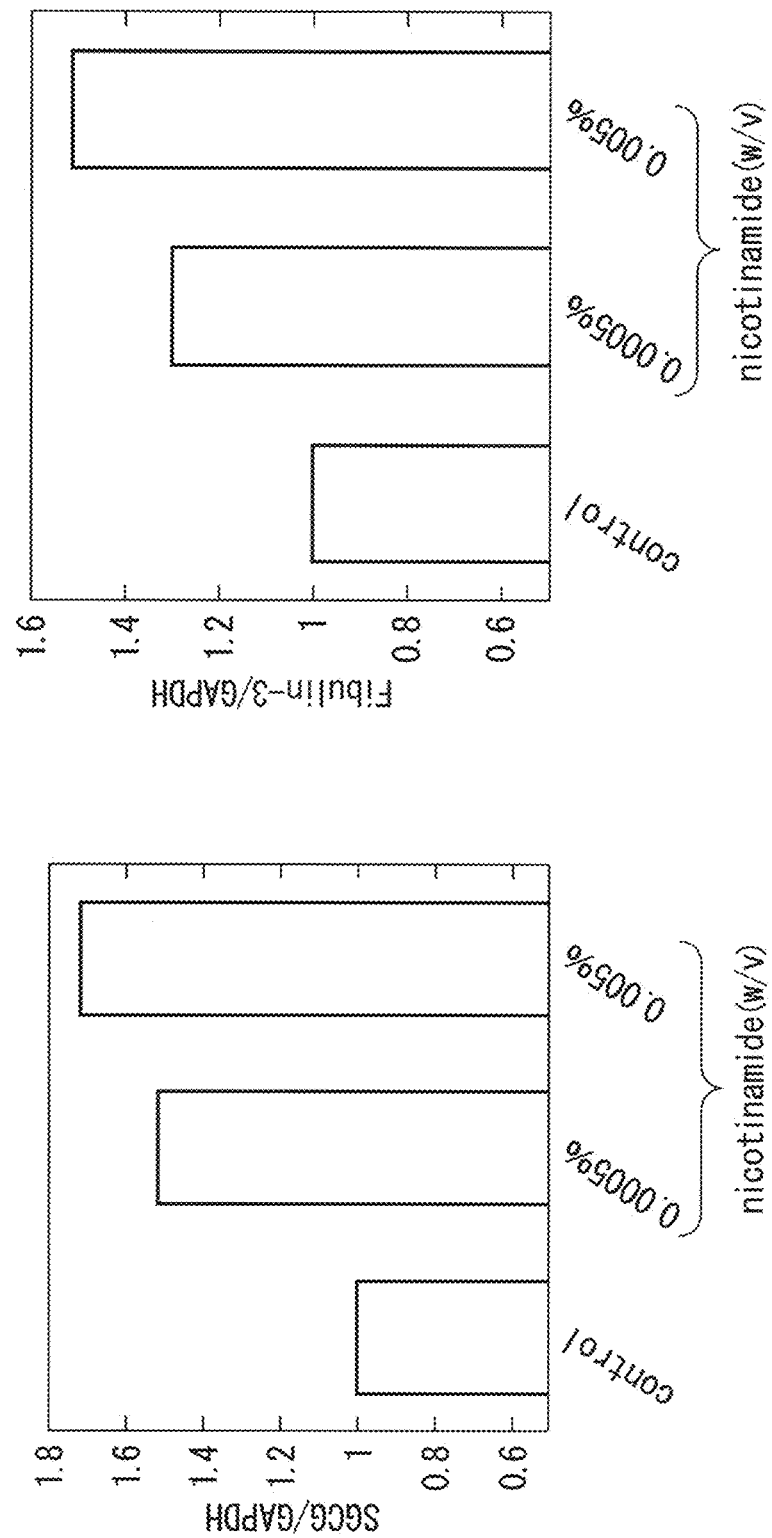
FIG. 8 is a drawing showing changes in the expression of sarcoglycan gamma and fibulin-3 when nicotinamide was added to cultured fibroblasts.

Fibroblasts derived from human skin tissue were plated in a 24-well type I collagen-coated dish (IWAKI), and cultured to 70-80% confluence in a 10% bovine fetal serum-supplemented DMEM (Gibco/Invitrogen) under the condition of 37° C. and 5% $CO_2$. After replacing with a serum-free medium for half a day, it was further replaced with a serum-free medium with varying concentrations of conjugated linoleic acid (Sigma) (0.001% v/v, 0.01% v/v) or nicotinamide (Sigma) (0.0005% v/v, 0.005% v/v). 24 hours later, RNA was recovered by using RNeasy mini kit (Qiagen) according to Qiagen's protocol. As a control, RNA prepared and recovered by substituting the medium with an intact serum-free medium, and recovering RNA 24 hours later was used. The concentration of the recovered RNA was determined using a nucleic acid quantitation instrument Nanodrop (Thermo Scientific). After adjusting the RNA concentration of the comparative control group at the same concentration, cDNA was synthesized from RNA using a cDNA synthesis kit High capacity cDNA reverse transcription kit (Applied Biosystems) according to an Applied Biosystems's protocol. Using a method described in Example 4, changes in the expression of fibulin-3 and the expression of sarcoglycan gamma when each known cellulite-improving drug was used are shown in FIG. 7 and FIG. 8.

Example 6

Sonication of Cultured Cells

Figure 9:
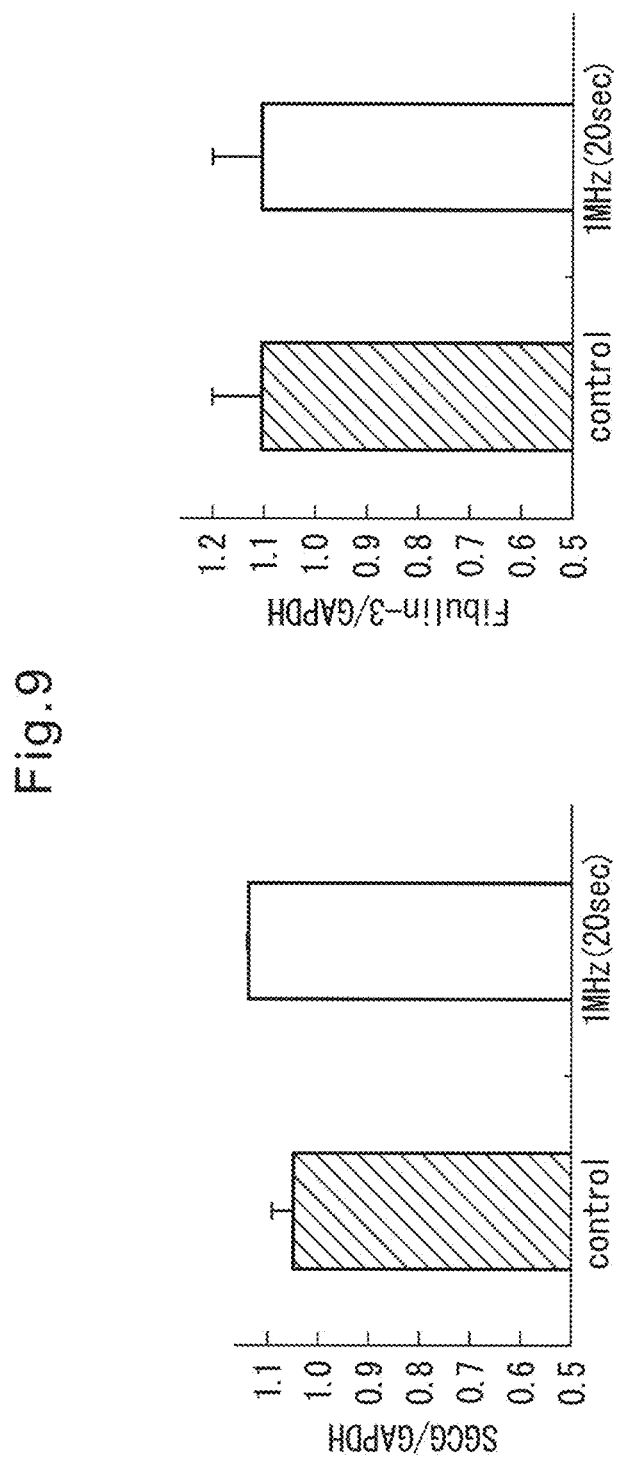
FIG. 9 is a drawing showing changes in the expression of sarcoglycan gamma and fibulin-3 when 1 MHz ultrasonic stimulation was applied to cultured fibroblasts.

Fibroblasts derived from human skin tissue were plated in a 35 mm well dish (Becton Dickinson), and cultured to 70-80% confluence in a 10% bovine fetal serum-supplemented DMEM (Gibco/Invitrogen) under the condition of 37° C. and 5% $CO_2$. After replacing with a serum-free medium for half a day, it was further replaced with a fresh serum-free medium, and subjected to 1 MHz ultrasonic stimulation at a distance of 0.5 mm using an ultrasonic cosmetic machine (Matsushita Denko). The stimulation time was set at a short 20 seconds, considering that the cells are directly stimulated. After 24 hours of stimulation, RNA was recovered according to Qiagen's protocol. The concentration of the recovered RNA was determined using a nucleic acid quantitation instrument Nanodrop (Thermo Scientific). After adjusting the RNA concentration of the comparative control group at the same concentration, cDNA was synthesized from RNA using a cDNA synthesis kit High capacity cDNA reverse transcription kit (Applied Biosystems) according to an Applied Biosystems's protocol. Using a method described in Working Example 4, changes in the expression of fibulin-3 and the expression of sarcoglycan gamma when sonication was carried out are shown in FIG. 9.

The invention claimed is:

1. A method of evaluating a drug for improving or treating cellulite, comprising the steps of:
    harvesting dermal fibroblast cells from human skin tissue by microdissection and culturing the dermal fibroblast cells;
    adding a candidate drug to the cultured dermal fibroblast cells;
    determining an expression level of fibulin-3 in the cultured dermal fibroblast cells after adding the candidate drug by quantitative PCR;
    comparing a control expression level of fibulin-3 with the determined expression level of fibulin-3 after adding the candidate drug; and
    determining that the candidate drug has a cellulite-suppressing activity when the determined expression level of fibulin-3 is enhanced compared to the control expression level of fibulin-3.

2. The method according to claim 1, wherein the determination that the candidate drug has a cellulite-suppressing activity requires that the determined expression of fibulin-3 is enhanced by 20% or more compared to the control expression level of fibulin-3.

3. The method of claim 2, wherein the enhancement is 35% or more.

4. The method of claim 2, wherein the enhancement is 50% or more.

5. The method of claim 1, wherein the quantitative PCR uses a primer selected from the group consisting of SEQ ID NOs: 5 and 6.

6. A method for screening a drug which has an activity for improving or treating cellulite, the method comprising:
    extracting dermal fibroblast cells from human skin tissue by microdissection and culturing the dermal fibroblast cells;
    providing a test sample of the cultured dermal fibroblast cells and a control sample;
    adding a candidate drug to the test sample of cultured dermal fibroblast cells;
    determining an expression level of fibulin-3 in each of a) the test sample after adding the candidate drug and b) the control sample by quantitative PCR;
    comparing the expression level of fibulin-3 determined in the control sample with the expression level of fibulin-3 determined in the test sample; and
    determining that the candidate drug has an activity for improving or treating cellulite when the expression level of fibulin-3 is increased in the test sample compared to the expression level of fibulin-3 in the control sample.

7. The method according to claim 6, wherein the determination that the candidate drug has an activity for improving or treating cellulite requires that the expression level of fibulin-3 in the test sample is enhanced by 20% or more compared to the expression level of fibulin-3 in the control sample.

8. The method of claim 7, wherein the enhancement is 35% or more.

9. The method of claim 7, wherein the enhancement is 50% or more.

10. The method of claim 6, wherein the quantitative PCR uses a primer selected from the group consisting of SEQ ID NOs: 5 and 6.

* * * * *